United States Patent

Fayram

[11] Patent Number: 5,545,189
[45] Date of Patent: Aug. 13, 1996

[54] CASE-ACTIVATING SWITCH ASSEMBLY FOR AN IMPLANTABLE CARDIAC STIMULATION DEVICE

[75] Inventor: Timothy A. Fayram, Gilroy, Calif.

[73] Assignee: Ventritex, Inc., Sunnyvale, Calif.

[21] Appl. No.: 552,039

[22] Filed: Nov. 2, 1995

[51] Int. Cl.[6] .................................................. A61N 1/00
[52] U.S. Cl. ................................................ 607/37; 607/36
[58] Field of Search ...................................... 607/37, 36, 4, 607/5

[56] References Cited

U.S. PATENT DOCUMENTS

| | | | |
|---|---|---|---|
| 4,142,532 | 3/1979 | Ware | 607/37 |
| 4,245,642 | 1/1981 | Skubitz et al. | 607/37 |
| 4,301,805 | 11/1981 | Peers-Trevarton, et al. | 128/419 |
| 4,445,511 | 5/1984 | Cowdery et al. | 607/37 |
| 4,727,877 | 3/1988 | Kallok | 128/419 |
| 4,922,927 | 5/1990 | Fine, et al. | 128/786 |
| 5,129,394 | 7/1992 | Mehra | 128/419 |
| 5,133,353 | 7/1992 | Hauser | 128/419 |
| 5,261,400 | 11/1993 | Bardy | 128/419 |
| 5,374,279 | 12/1994 | Duffin, Jr. et al. | 607/5 |

*Primary Examiner*—William E. Kamm
*Assistant Examiner*—Carl H. Layno
*Attorney, Agent, or Firm*—Steven M. Mitchell; Mark J. Meltzer

[57] ABSTRACT

A switch assembly for an implantable cardiac stimulation device which enables the implanting physician to selectively activate the pulse generator case or can of the device and/or to selectively activate an endocardial lead electrode inserted into a lead connector cavity or bore thereof. Also disclosed is an implantable cardiac stimulation device, e.g., an implantable cardioverter/defibrillator, which includes one or more such switch assemblies, to thereby enable the implanting physician to select any of a number of different electrode configuration options. For example, if two switch assemblies are used, the implanting physician is afforded six options.

30 Claims, 4 Drawing Sheets

CASE-ACTIVATING SWITCH ASSEMBLY FOR AN IMPLANTABLE CARDIAC STIMULATION DEVICE

BACKGROUND OF THE INVENTION

The present invention relates generally to implantable cardiac stimulation devices, such as pacemakers and implantable cardioverter-defibrillators (ICDs), and, more particularly, to a switch assembly for an implantable cardiac stimulation device which can be selectively configured to electrically connect the case (can) of the device to either a positive or negative polarity high voltage defibrillator output, to thereby electrically "activate" the can so that it can serve as an electrode of the chosen polarity.

Various types of implantable cardiac stimulation devices are presently available for delivering various types of cardiac stimulation therapy. The two most common types which are in widespread use are pacemakers and ICDs. Pacemakers generally produce relatively low voltage pacing pulses which are delivered to the patient's heart through low voltage, "bipolar" pacing leads, generally across spaced-apart ring and tip electrodes thereof which are of opposite polarity. These pacing pulses assist the natural pacing function of the heart in order to prevent bradycardia. Contemporary ICDs are capable of delivering tiered therapy, e.g., bradycardia pacing therapy, antitachycardia pacing therapy, cardioversion therapy, and defibrillation therapy. Each tier or level of therapy requires the delivery of pulses of progressively higher voltage.

Early generation ICDs utilized a lead system which consisted of at least one epicardial patch electrode of a first polarity which was sewn onto the surface of the patient's heart, in combination with another epicardial patch electrode of a second polarity or a transvenous electrode of a second polarity placed in the region of the patient's superior vena cava. A thoracotomy procedure (i.e., a surgical opening of the patient's chest) was required to implant the epicardial patch electrodes.

Fortunately, lead systems have been developed which eliminate the necessity of a thoracotomy. Although there are a variety of different such nonthoracotomy lead systems which are presently known, most contemporary systems utilize a combination of a right ventricular (RV) endocardial lead electrode placed in the apex of the right ventricle of the patient's heart, a superior vena cava (SVC) transvenous lead electrode placed in the region of the SVC of the patient's heart, and, if necessary, a subcutaneous (SubQ) electrode (located underneath the patient's skin in the left chest area). Of course, at least two of these "unipolar" lead electrodes are of opposite polarity. Where two defibrillation electrodes of the same polarity are used, a "Y" adapter may be used to couple both electrodes to a single connector port.

Such nonthoracotomy lead systems can be implanted by the physician at the time that the ICD is implanted, using minimally invasive techniques, e.g., guiding the leads through veins in the upper chest down inside the patient's heart. The SubQ electrode can be a subcutaneous patch electrode, and/or, a conductive portion of the housing or can of the ICD can be used as a SubQ electrode. When the conductive portion of the can is used as an electrode (i.e., electrically connected to a high voltage terminal of the pulse generator circuitry of the ICD), the can is considered "active", and thus, is commonly referred to as an "active can". If not, the can is considered "inactive" or "passive".

Systems that deliver a defibrillation pulse between one or more endocardial electrodes and an active defibrillator housing are disclosed in U.S. Pat. Nos. 4,727,877, issued to Kallok; 4,922,927, issued to Fine et al.; 5,129,394, issued to Mehra; 5,133,353, issued to Hauser; 5,261,400, issued to Bardy; and, 5,374,279, issued to Duffin, Jr. et al., all of which are herein incorporated by reference. As used herein, the terms "housing", "enclosure", "case", and "can" are synonymous.

If the implanting physician chooses to use an active can which is pectorally implanted, it is unlikely that this decision would be changed in the future. If the implanting physician chooses to use a SubQ lead electrode and an inactive can which is abdominally implanted, it is also unlikely that this decision would be later changed. Even if this decision were reversed (i.e., if it were later decided to activate the can), a surgical procedure would likely be required in order to reposition the can for effective use as an electrode. Therefore, external programmability of this choice of active or inactive can is not needed, thereby allowing the design and manufacture of the ICD to be less complex.

In this connection, an ICD which would afford the implanting physician the capability of choosing from a number of different electrode configurations, including can active or inactive, at the time of implant, would be highly beneficial, as such electrode configuration selectability would enable the implanting physician to optimize the defibrillation threshold (DFT), which is the minimum amount of energy required to defibrillate a patient's heart, and thus optimize the defibrillation therapy delivered by the ICD for that patient.

In U.S. Pat. No. 4,301,805, issued to Peers-Trevarton et al., a cardiac pacer connector system is disclosed that is provided with a bridging means for using the pacer case as a reference potential when a unipolar lead is used. When a bipolar pacing/sensing lead is used the bridging means is not operated, and the pacer case is inactive.

In U.S. patent application Ser. No. 08/455,824, filed on May 31,1995 which is a Continuation-In-Part of application Ser. No. 08/221,811, filed Mar. 31, 1994 and abandoned on Oct. 31, 1995, in the name of Pless et al., which is assigned to the assignee of the present in cardiac defibrillator with a case that can be made electrically active or inactive is disclosed. A special connector cavity is provided that has one terminal electrically connected to the pulse generator case and a second terminal connected to one pole of the defibrillator output. By plugging in a pin long enough to contact both terminals, the case is activated during delivery of a defibrillation shock. No means is disclosed therein for using a standard connector pin, such as a DF-1 defibrillator connector pin. The device disclosed in U.S. Pat. No. 5,374, 279, issued to Duffin, Jr. et al., has a similar deficiency in that a special lead connector or plug must be provided to activate the defibrillator case.

Because of the desire to be compatible with existing lead connectors without requiring a special adapter, both at initial implant and during a pulse generator replacement, it would be useful if the pulse generator case could be activated while allowing the use of standard lead connectors.

U.S. patent application Ser. No. 463,527, filed Jun. 5, 1995, in the name of Paspa et al., which is assigned to the assignee of the present invention, the disclosure of which is herein incorporated by reference, discloses a state-of-the-art defibrillator which is provided with a header which includes means for enabling the implanting physician to quickly, safely, and easily select the can to be active (either polarity) or inactive, by merely tightening or not tightening either or both of two setscrews into respective setscrew cavities provided in the header. Similarly, lead connectors (e.g., of RV and SVC lead electrodes) can be selectively inserted or plugged into standard lead connector cavities provided in the header, and setscrews selectively tightened onto the lead connector pins thereof, to thereby selectively activate the inserted lead electrodes. By this simple technique, various electrode configurations can be easily selected to thereby provide the optimum system for a given patient. The defibrillator of this invention is simpler and safer to manufacture and implant than previously known defibrillators, and can be used with previously implanted defibrillation leads. Further, the defibrillator of this invention allows the use of standard lead connectors without requiring a special adapter or a lead having a special connector.

U.S. patent application Ser. No. 353,422, filed Dec. 9, 1994, in the name of Paul Paspa, which is assigned to the assignee of the present invention, the disclosure of which is herein incorporated by reference, discloses another state-of-the-art defibrillator which is provided with a header which includes means for enabling the implanting physician to quickly, safely, and easily select the can to be active or inactive, and/or a lead electrode(s) to be active or inactive, by merely tightening or not tightening either or both of two setscrews into respective setscrew cavities provided in the header. Similarly, lead connectors (e.g., of RV and SVC lead electrodes) can be selectively inserted or plugged into standard lead connector cavities provided in the header, and setscrews selectively tightened onto the lead connector pins thereof, to thereby selectively activate the inserted lead electrodes. By this technique, various electrode configurations can be easily selected to thereby provide the optimum system for a given patient. The defibrillator of this invention is also simpler and safer to manufacture and implant than previously known defibrillators, and can also be used with previously implanted defibrillation leads. Further, the defibrillator of this invention also allows the use of standard lead connectors without requiring a special adapter or a lead having a special connector.

The present invention is directed to an implantable cardiac stimulation device, and a novel switching assembly therefor, which affords the full range of easily selectable electrode configuration options, an which is an alternative to the above-referenced state-of-the-art defibrillators, and which provides certain advantageous features not found in such state-of-the-art defibrillators. These advantageous features, which will become apparent hereinafter, are believed to enhance the manufacturability and reliability of the device.

SUMMARY OF THE INVENTION

The present invention encompasses a switch assembly for an implantable cardiac stimulation device which enables the implanting physician to selectively activate the pulse generator case or can of the device and/or to selectively activate an endocardial lead electrode inserted into a lead connector cavity or bore thereof. The switch assembly includes a first electrically conductive connector block having a first portion and a second portion, the first portion having a connector bore and a first hole transverse to and connected to the connector bore, an electrically insulative housing extending outwardly from the second portion of the first connector block, an electrically conductive element disposed within the housing and electrically coupled to the first connector block, a push block disposed within the housing, at least a portion of the push block being electrically conductive, wherein the push block is movable from a first position in which the electrically conductive portion is not in contact with the electrically conductive element, and a second position in which the electrically conductive portion is in contact with the electrically conductive element, and a second electrically conductive connector block having a second hole in communication with the push block. The first and second connector blocks are electrically insulated from each other when the push block is in the first position, and are electrically coupled to each other when the push block is in the second position. The first connector block is electrically coupled to a high voltage terminal (of either polarity) of the pulse generator circuitry of the device, and the second connector block is electrically coupled to an electrically conductive portion of the pulse generator housing or can.

A first option for the implanting physician is to insert or plug in a lead connector of an endocardial, transvenous, or subcutaneous lead electrode (e.g., an RV, SVC, or SubQ lead electrode) into the connector bore provided in the first portion of the first connector block, and tighten a first setscrew into the first hole to contact the lead connector pin, to thereby activate the inserted lead electrode. With the first option, the implanting physician can either elect to activate the can or leave it inactivated (passive), thus effectively presenting the implanting physician with a second option. The implanting physician can activate the can by inserting an electrically conductive connector element, e.g., a second setscrew or conductive plug, into the second hole provided in the second connector block which is long enough move the push block from the first position to the second position. If the implanting physician elects to keep the can inactive, it is preferable that the implanting physician insert a seal screw or plug to form a fluid seal to prevent the intrusion of fluids, bacteria, and other contaminants into the second hole. A third option for the implanting physician is to insert a conductive plug or connector element into the connector bore and tighten the first and second setscrews, to thereby activate the can. A fourth option for the implanting physician is to insert a first plug, preferably a nonconductive plug, into the connector bore and tighten the first setscrew (to mechanically stabilize the plug) and insert a seal screw or second plug into the second hole provided in the second connector block which is not long enough to move the push block from the first position to the second position. With the fourth option, the first and second plugs serve to seal the connector bore and first and second holes against fluids, bacteria, and other contaminants. Since bodily fluids are electrically conductive, they could potentially cause a short circuit if allowed into the first and second holes.

In a presently preferred embodiment of the present invention, the electrically conductive element is an electrically conductive post and the push block is a plastic block provided with a central recess and a conductive pad seated in the central recess. A central aperture having a diameter greater than that of the post is provided in the push block in order to allow the push block to slide along the post when it is moved from the first position to the second position, whereby the conductive pad is brought into contact with the post. Further, a preloaded spring is preferably provided in surrounding relationship to the post between the push block and a conductive stop member secured to the second portion of the first connector block. The spring acts to exert an upwardly directed biasing force against the push block which urges the push block into the first position, in the absence of an opposing force, i.e., when the case-activating setscrew or plug is not inserted into the second hole.

In essence, the push block and post function like a switch. More particularly, the push block functions like a movable contact and the post as a fixed contact, with the spring functioning to maintain the switch in a normally open position. When it is desired to close the switch in order to electrically activate the can, a case-activating screw (or other suitable electrically conductive connector element) is screwed into the second hole and tightened, in order to thereby overcome the upwardly directed biasing force of the spring and thus move the push block into electrical contact with the post.

Additionally, the second hole is preferably internally threaded, whereby the upwardly directed biasing force exerted by the spring against the push block produces a frictional, anti-rotational engagement between the mating surfaces of the external threads of the case-activating setscrew and the internal threads of the second hole, when the switch is in the "on" position (i.e., the movable contact element or push block is in its second position, in which it is in contact with the post or fixed contact element). This frictional, anti-rotational engagement between the mating surfaces of the external threads of the case-activating setscrew and the internal threads of the second hole prevents loosening of the case-activating setscrew over time and/or in response to mechanical stresses and vibration, thus preventing inadvertent opening of the switch (i.e., inadvertent movement of the push block from the second position to the first position, in which it is not in contact with the post), and further, ensuring good electrical contact between the external threads of the case-activating setscrew and the internal threads of the second hole. In this regard, the upwardly directing biasing force exerted by the spring against the push block produces an effect similar to that provided by the action of a lock washer.

The present invention also encompasses an implantable cardiac stimulation device, e.g., an ICD, which includes one or more such switch assemblies, to thereby enable the implanting physician to select any of a number of different electrode configuration options. For example, if two switch assemblies are used, the implanting physician is afforded six options. In this way, the implanting physician can choose the optimum electrode configuration for a given patient, without having to bring two or more different defibrillators into the operating room, e.g., one having an active can and another having an inactive can, and without requiring the manufacturer or physician to program the device.

BRIEF DESCRIPTION OF THE DRAWINGS

The above and other objects, features, and advantages of the present invention will be more clearly understood from the following detailed description taken in conjunction with the accompanying drawings, in which:

FIG. 2B is a top, sectional view of a case-activator switch assembly with the switch on;

DETAILED DESCRIPTION OF THE INVENTION

Figure 1:
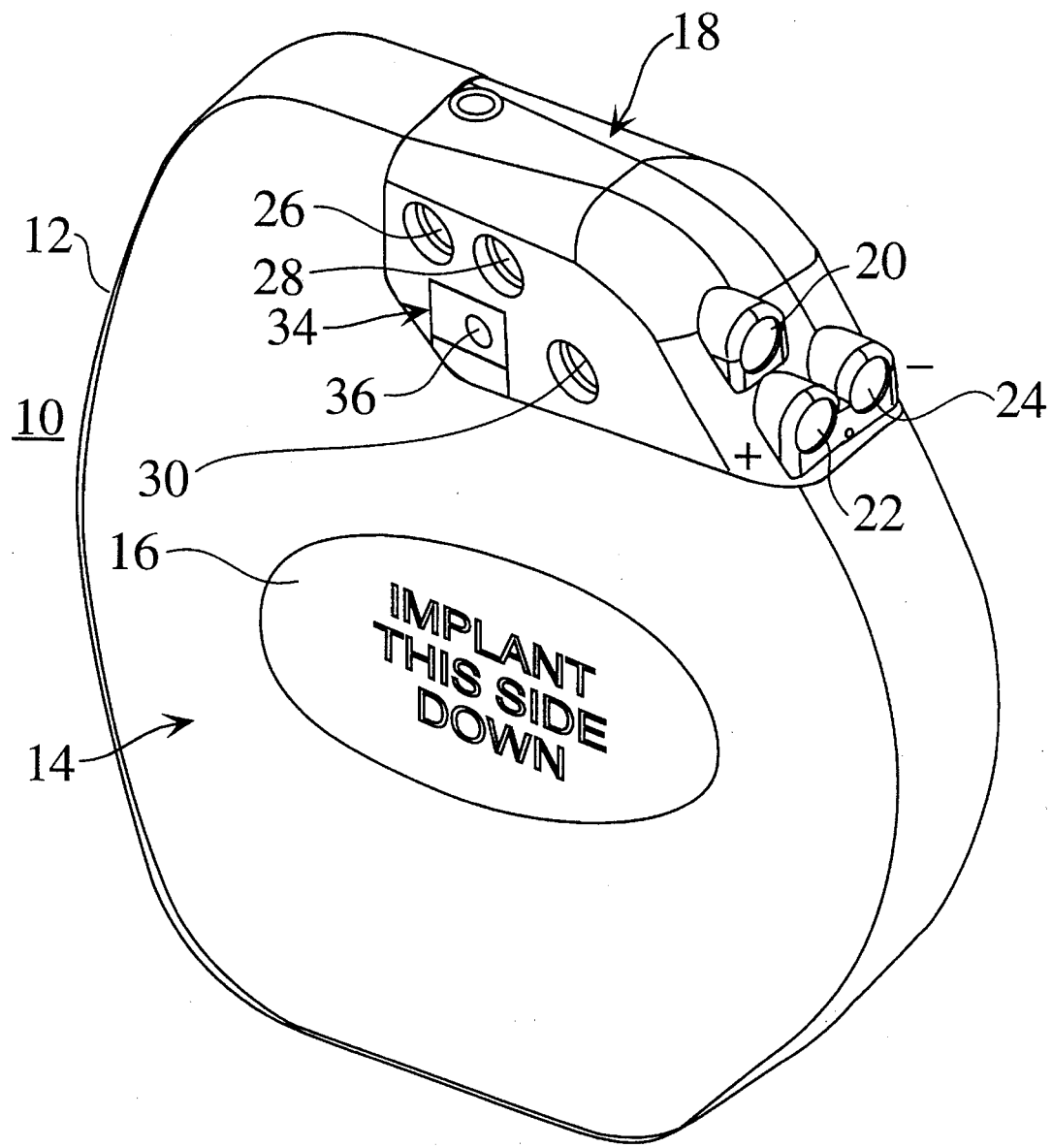
FIG. 1 is a perspective view of an implantable cardiac stimulation device constructed in accordance with a presently preferred embodiment of the present invention.

With reference now to FIG. 1, there can be seen an implantable cardiac stimulation device 10 constructed in accordance with a presently preferred embodiment of the present invention. The device 10 of the presently preferred embodiment is an implantable cardioverter-defibrillator (ICD) which is capable of delivering tiered therapy, e.g., anti-bradycardia pacing therapy, anti-tachycardia pacing therapy, cardioversion therapy, and defibrillation therapy. For ease of description, the device 10 will hereinafter be referred to as the pulse generator 10. The housing 12 of the pulse generator 10 will hereinafter be referred to as the pulse generator case or can 12. The pulse generator can 12 houses the pulse generator circuitry (not shown) of the device, and is typically constructed of titanium, although any other corrosion-resistant, biocompatible electrically conductive material may be used instead. The pulse generator can 12 may be partially insulated by a polymeric coating 14, with an exposed, electrically conductive portion 16 which may serve as an electrode when the can is electrically activated. The polymeric insulating coating 14 serves to keep current flow between electrodes focused toward the heart during delivery of a defibrillation shock, so as to lower the defibrillation threshold (DFT) and to avoid undesirable skeletal muscle stimulation. Alternatively, the entire surface of the pulse generator can 12 may be left uncoated, and therefore electrically conductive. The outer surface of the pulse generator can 12 may be of any desired shape or configuration to facilitate its discharge capabilities. Alternative means for insulating the can 12 may also be used, such as an electrically insulative, biocompatible boot (not shown) having a cutout.

A header 18, which is preferably made of transparent or translucent polymeric material, such as epoxy or a thermoplastic elastomer, is attached or secured to the can 12. It should be noted that the terms "attached" and "secured" are used hereinthroughout in their broadest possible sense, e.g., two parts can be attached or secured together by means of being press fit, welded, glued, or screwed together, or may be integrally formed or attached, e.g., machined from a unitary workpiece. For example, as used above, the header 18 can either be formed separately and then attached to the can 12, or can be formed in situ or built into the can 12. In the presently preferred embodiment of the present invention, the header 18 is provided with three lead connector cavities or bores 20, 22, and 24, which can be thought of as tunnels in the header 18. The header 18 is also provided with threaded setscrew holes or cavities 26, 28, and 30. A fourth threaded setscrew hole or cavity (not shown) is provided in the header 18 opposite the setscrew cavity 30. The header 18 is also provided with a case-activation switch assembly 34 constructed in accordance the present invention. The header 18 is also preferably provided with another case-activation switch assembly (not shown) identical to and opposite from the case-activation switch assembly 34 (but rotated 180° relative thereto).

The lead connector cavity 20 is preferably a bipolar pacing lead connector cavity of a standard type, e.g., of the IS-1BI type described in ISO 5841-3:1992(E) "Cardiac pacemakers—Part 3: Low-profile connectors (IS-1) for implantable pacemakers" (International Standard). A bipolar pacing lead (not shown) can be electrically activated at the time of implant by inserting or plugging the lead connector portion thereof into the bipolar pacing lead connector cavity 20 and then tightening setscrews (not shown) into the setscrew cavities 26, 28 and into contact with the pacing lead connector pin, through a connector block (not shown), in the normal manner. The bipolar pacing lead may suitably be of a conventional type, e.g., one with a ring electrode connected to a first polarity pacing voltage terminal of the pulse generator circuitry, and a tip electrode connected to an opposite polarity pacing voltage terminal of the pulse generator circuitry. Alternatively, the header 18 may include a pair of pacing lead connector cavities for use with two lead connectors of a bipolar bifurcated lead, or other configurations, as are well-known in the art.

The lead connector cavities 22, 24 are preferably unipolar defibrillator lead connector cavities of a standard type, e.g., of the DF-1 type described in ISO 11318:1993(E) "Cardiac defibrillators—Connector assembly for implantable defibrillators—Dimensional and test requirements" (International Standard). The unipolar defibrillator lead connector cavities 22, 24 are of opposite polarity, e.g., (+) and (−), respectively. Two unipolar defibrillator lead electrodes (not shown), e.g., RV and SVC (or SubQ) lead electrodes, can be electrically activated at the time of implant by inserting or plugging the lead connector portions thereof into the unipolar defibrillator lead connector cavities 22, 24 of the desired polarity, and then tightening setscrews (not shown) into the setscrew cavity 30 and the opposite setscrew cavity (not shown), respectively, and into contact with the respective lead connector pins, through respective unipolar lead connector blocks (not shown), in the normal manner. In the presently preferred embodiment of the present invention, the unipolar lead connector blocks are part of the case-activation switch assembly 34 and the opposite case-activation switch assembly (not shown), respectively, as will become fully apparent hereinafter.

Additionally, the pulse generator can 12 can be electrically activated to either polarity by inserting or plugging either a unipolar lead connector or conductive plug into the unipolar defibrillation lead connector cavity 22 or 24 of the desired polarity (if not already inserted), and then tightening a special case-activating setscrew 80 (see FIG. 5) into the case-activation setscrew hole or cavity 36 of the case-activation switch assembly 34 or the case-activation setscrew hole or cavity (not shown) of the opposite case-activation switch assembly (not shown), through a respective case-activation connector block (not shown), in a manner hereinafter fully described. In the presently preferred embodiment of the present invention, the case-activation connector blocks are part of the case-activation switch assembly 34 and the opposite case-activation switch assembly (not shown), respectively, as will also be fully described hereinafter. The case-activation connector blocks are both electrically coupled to the electrically conductive portion 16 of the pulse generator can 12.

Figure 2A:
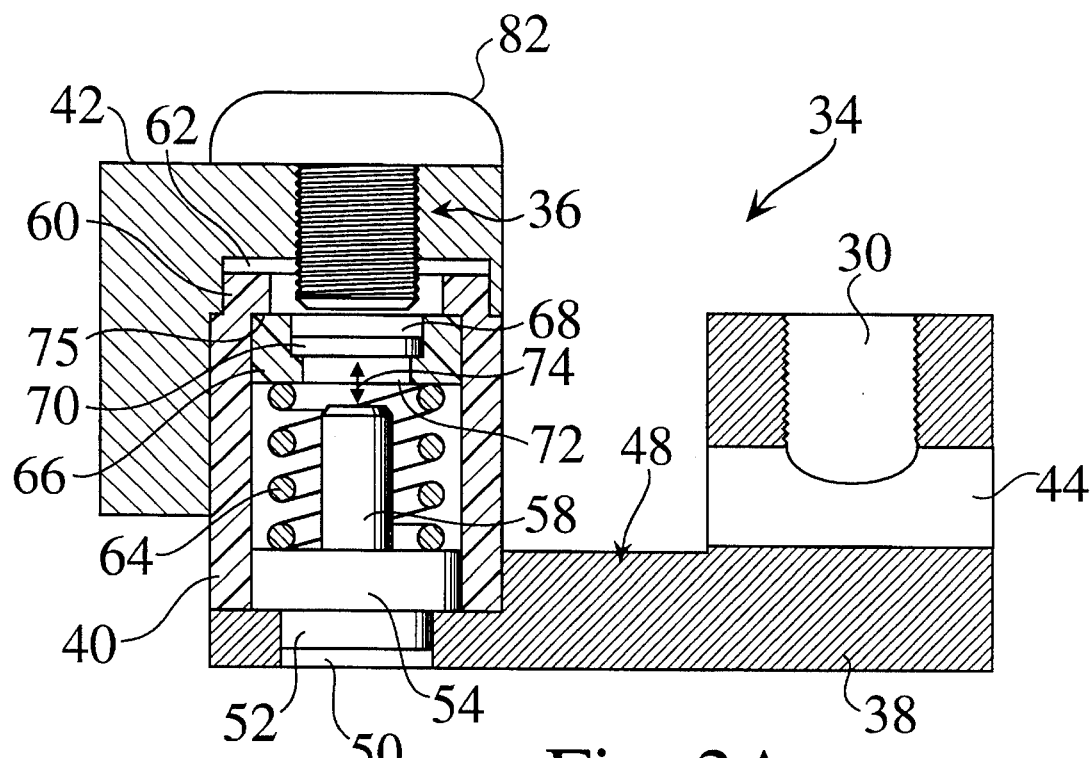
FIG. 2A is a top, sectional view of a case-activator switch assembly with the switch off constructed in accordance with a presently preferred embodiment of the present invention.
Figure 2B:
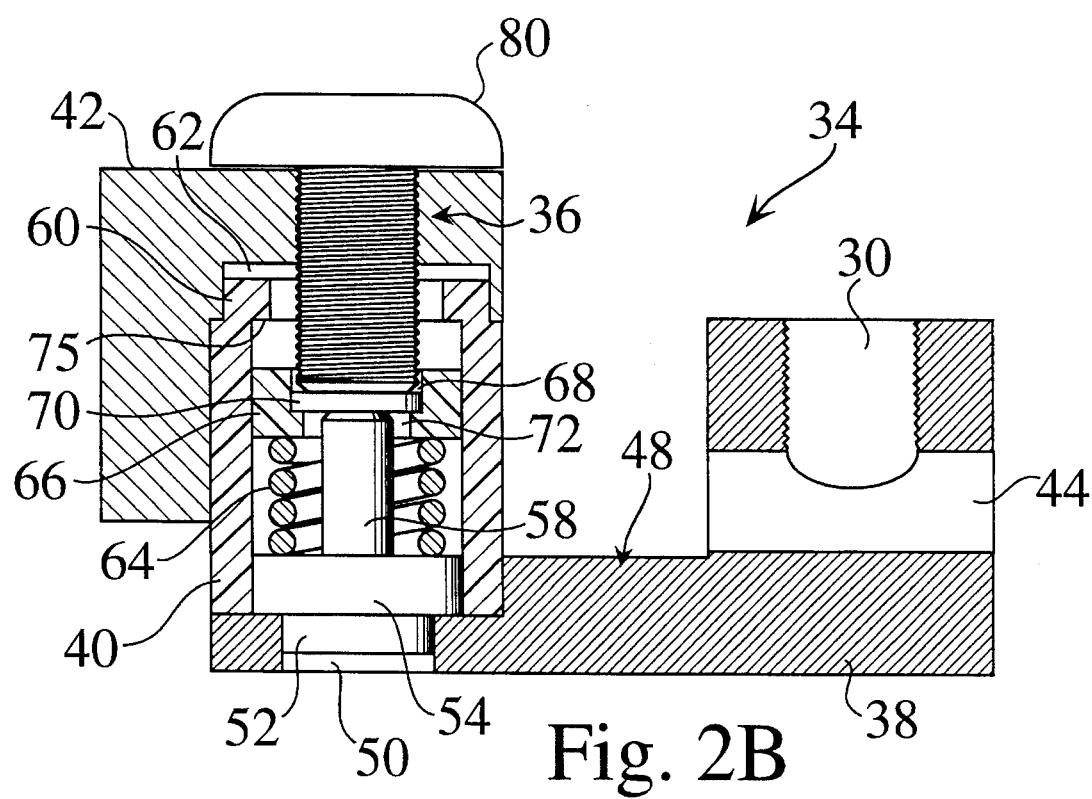
Figure 3:
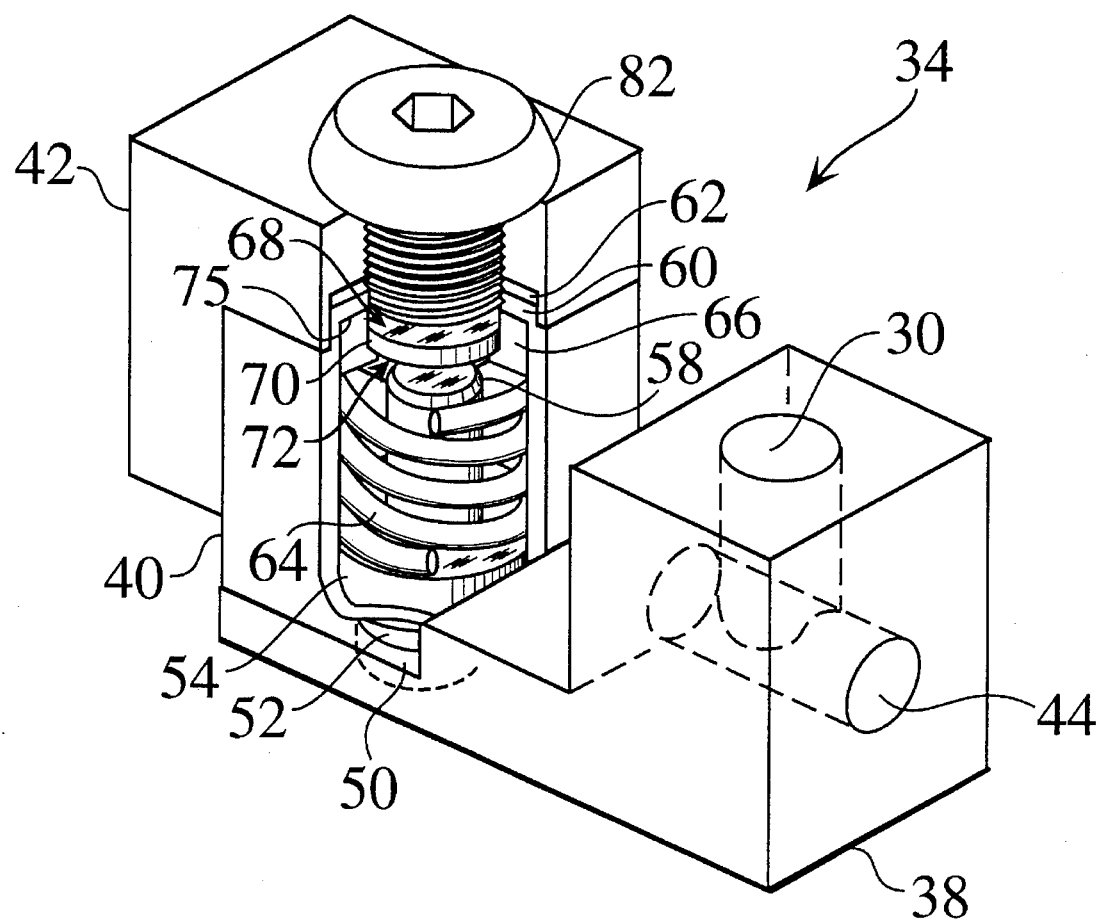
FIG. 3 is a partially cut away perspective view of a case-activator switch assembly constructed in accordance with a presently preferred embodiment of the present invention.
Figure 4:
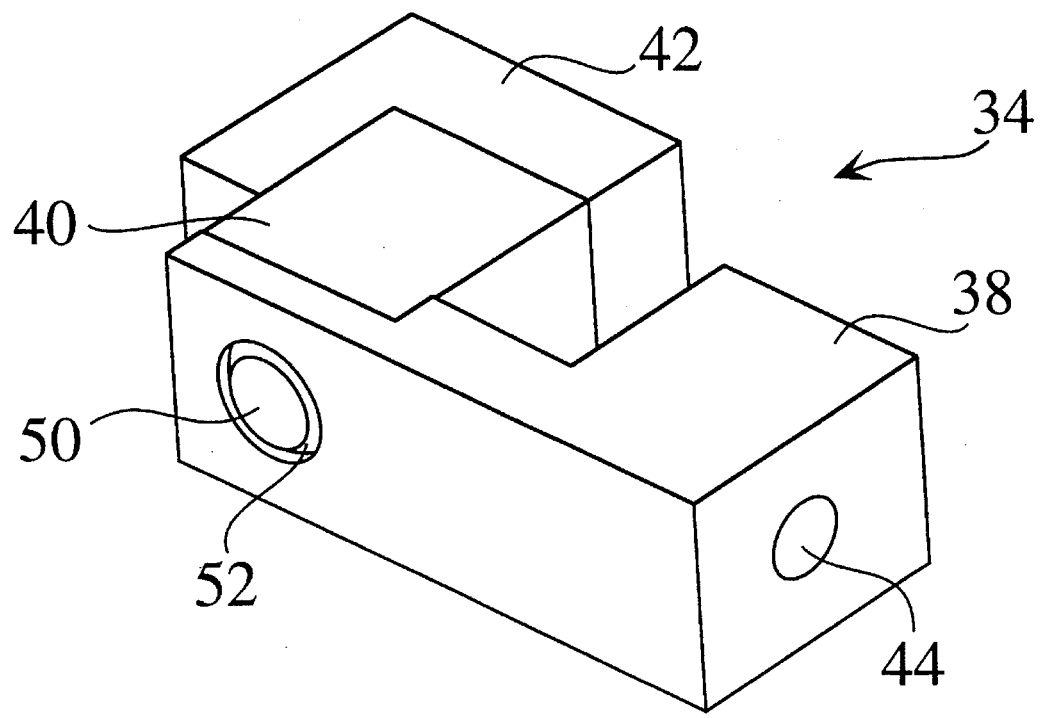
FIG. 4 is a perspective view of the case-activator switch assembly of the present invention depicted in FIG. 2 and FIG. 3; and, FIG. 5 is an elevational, partially sectional view of a case-activation setscrew of the present invention.

With reference now to FIGS. 2A, 2B and 3, there can be seen a presently preferred embodiment of the case-activation switch assembly 34 of the present invention. In overview, the case-activation switch assembly 34 includes an electrically conductive lead connector block 38, an electrically insulative housing 40, and an electrically conductive case-activation connector block 42 which are attached or secured together in such a manner as they fit tightly together and form a fluid-tight seal. The conductive lead connector block 38 is electrically coupled to a high voltage terminal, e.g., (+) defibrillator output terminal, of the pulse generator circuitry of the implantable cardiac stimulation device 10, e.g., by means of a platinum feedthrough wire or other type of electrical conductor (not shown) resistance welded or otherwise attached to the conductive lead connector block 38. The case-activation connector block 42 is electrically coupled to the electrically conductive portion 16 of the pulse generator can 12, e.g., by means of a platinum wire or other type of electrical conductor (not shown) one end of which is resistance welded or otherwise attached to the case-activation connector block 42 and the other end of which is resistance welded or otherwise attached to the electrically conductive portion 16 of the pulse generator can 12.

The lead connector block 38 includes a lead connector cavity or bore 44 which is axially aligned with and in communication with the defibrillation lead connector cavity 22 for receiving the lead connector pin (not shown) of a unipolar defibrillation lead (not shown), e.g., an RV, SVC, or SubQ lead, inserted or plugged into the unipolar defibrillation lead connector cavity 22. In this regard, the lead connector bore 44 constitutes a distal portion of the defibrillation lead connector cavity 22. The lead connector block 38 is preferably constructed of titanium, although any other suitable machinable, corrosion-resistant, biocompatible, electrically conductive material can be employed instead.

The lead connector block 38 also includes the internally threaded setscrew hole or cavity 30 which is transverse to and connected with the lead connector bore 44. In the presently preferred embodiment, the lead connector block 38 includes a laterally outwardly extending wing or flange portion 48 which is provided with a hole or recess 50 into which a downwardly depending boss or connector portion 52 of an electrically conductive stop member 54 is press-fit. The stop member 54 is preferably constructed of titanium, although any other suitable machinable, corrosion-resistant, biocompatible, electrically conductive material can be employed instead. The stop member 54 is preferably a cylindrical shape with a cylindrical rod or post 58 upwardly extending from stop member 54.

The electrically insulative housing 40 is preferably constructed of a suitable plastic material, e.g., delrin, nylon or polyester, although any other suitable, corrosion-resistant, biocompatible, electrically insulating material can be used instead. The insulative housing 40 preferably has an upper boss or connector portion 60 which is press-fit into a corresponding cavity or recess 62 provided in the case-activation connector block 42, and a lower portion that is press-fit around the stop member 54. The housing 40 houses the post 58, an electrically conductive (e.g., stainless steel), preloaded spring 64 surrounding the post 58, and a plunger element or push block 66 captured between the spring 64 and an abutting surface 75 of the case-activation connector block 42.

The push block 66 is preferably constructed of a suitable plastic material, e.g., delrin, nylon or polyester, although any other suitable, corrosion-resistant, biocompatible, electrically insulating material can be used instead. The push block 66 includes a central recess 68 into which is press-fit an electrically conductive (e.g., titanium) button or pad 70, and a central aperture 72 which exposes at least a portion of the inner surface of the conductive pad 70 which faces the post 58. The central aperture 72 has a diameter greater than that of the post 58 in order to allow the push block 66 to slide up and down along the post 58, as indicated by the double-headed arrow 74. Further, the diameter of the central aperture 72 is preferably less than that of the central recess 68 in order to form a ledge or shoulder around the periphery of the central aperture 72 onto which the conductive pad 70 is seated. The spring 64 exerts an upwardly directed biasing force against the push block 66 which forces the push block 66 into a first position (as shown in FIGS. 2A and 3) in which there exists a gap between the conductive pad 70 and the post 58, in the absence of an opposing force. The upwardly directed biasing force exerted by the spring 64 also forces the push block 66 into firm engagement with the abutting surface 75 of the case-activation connector block 42, thus ensuring that a fluid-tight seal is formed between the push block 66 and the abutting surface 75 of the case-activation connector block 42. This fluid seal is important because if bodily fluids were to enter the internal cavity of the insulative housing 40, these fluids could create an electrical path and short out the switch assembly.

The case-activation connector block 42 is preferably constructed of titanium, although any other corrosion-resistant, biocompatible electrically conductive material may be used instead. The case-activation setscrew hole or cavity 36 is provided in the case-activation connector block 42 in axial alignment with the internal cavity of the insulative housing 40. The case-activation setscrew hole 36 is internally threaded to receive either a seal screw (switch-off screw) 82 (as shown in FIG. 2A) or the case-activating setscrew (switch-on) 80 (as shown in FIG. 2B). The seal screw 82 is preferably constructed of plastic, e.g., delrin, nylon, or polyester, or any other suitable electrically insulating, biocompatible material. The seal screw 82 is inserted into the case-activation setscrew hole 36 and tightened in order to provide a fluid-tight seal to prevent the intrusion of fluids, bacteria, and other contaminants into the case-activation setscrew hole 36, and a redundant, fluid-tight seal against intrusion of fluids into the internal cavity of the insulative housing 40. In the presently preferred embodiment, the seal screw 82 includes a metal hex insert (not shown) in the head thereof in order to enable the seal screw 82 to be tightened using a torque wrench without stripping the hex head.

Figure 5:
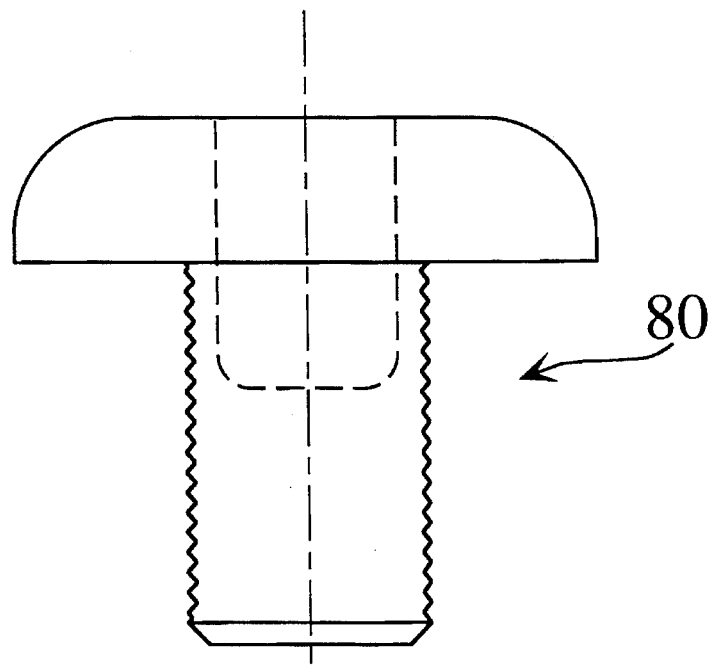

The seal screw 82 is used when it is not desired to electrically activate the pulse generator can 12, i.e., when it is desired to have the pulse generator can 12 be inactive (passive). In this regard, the seal screw 82 is not long enough to move the push block 66 from its first position to a second position in which the conductive pad 70 thereof contacts the post 58. When the push block 66 is in its first position, i.e., not in contact with the post 58, the switch assembly is in its "OFF" condition (state), as is depicted in FIGS. 2A and 3. When it is desired to electrically activate the pulse generator can 12, the case-activating setscrew 80 is inserted into the case-activating setscrew hole 36 and tightened as is depicted in FIGS. 2B. The case-activating setscrew 80, which is also shown in FIG. 5, is long enough so that when it is tightened it forces the push block 66 from its first position to its second position, i.e., it forces the conductive pad 70 into contact with the post 58, thereby switching the switch assembly to its "ON" condition (state). The physician will turn the case-activating setscrew 80 with a torque wrench that stalls or clicks at a torque of approximately 15 in-oz. The physician will then know that the case-activating setscrew is properly installed. When the switch assembly is in its "ON" state, the upwardly directed biasing force exerted by the spring 64 against the push block 66 produces a frictional, anti-rotational engagement between the mating surfaces of the external threads of the case-activating setscrew 80 and the internal threads of the case-activating setscrew hole 36 which prevents loosening of the case-activating setscrew 80 over time and/or in response to mechanical stresses and vibration, thus preventing inadvertent opening of the switch, i.e., inadvertent movement of the push block 66 from its second position to its first position, and further, ensuring good electrical contact between the external threads of the case-activating setscrew 80 and the internal threads of the case-activating setscrew hole 36. In this regard, the upwardly directed biasing force exerted by the spring 64 against the push block 66 produces an effect similar to that provided by the action of a lock washer.

In essence, the push block 66 and the post 58 function like a switch. More particularly, the push block 66 functions like a movable contact and the post 58 functions like a fixed contact, with the spring functioning to maintain the switch in the normally open position. When it is desired to close the switch in order to electrically activate the pulse generator can 12, the case-activating screw 80 (or other suitable electrically conductive connector element) is screwed into the case-activation setscrew hole 36 and tightened, to thereby overcome the upwardly directed biasing force exerted by the spring 64 and thus move the movable contact into contact with the fixed contact, to thereby close the switch.

With the case-activation switch assembly 34 depicted in FIGS. 2A, 2B and 3, the implanting physician is provided with four electrode configuration options. A first option is to insert or plug in a lead connector pin of a lead electrode into the lead connector bore 44, insert a setscrew (not shown) into the setscrew cavity 30 to contact the lead connector pin, to thereby activate the inserted lead electrode. With the first option, the implanting physician can either elect to activate the pulse generator can 12 or leave it inactivated (passive), thus effectively presenting the implanting physician with a second option. The implanting physician can activate the can 12 by inserting the case-activation setscrew 80 into the case-activation setscrew cavity 36 and then tightening it, in the manner described hereinabove. If the implanting physician elects to keep the can 12 inactive, it is preferable that the seal screw 82 be inserted into the case-activation setscrew cavity 36 and then tightened, in the manner described hereinabove. A third option for the implanting physician is to insert a conductive plug or connector element (not shown) into the lead connector bore 44 and then tighten the case-activation setscrew 80 and a setscrew (not shown) in the setscrew cavity 30, thereby activating the can 12 without activating a lead electrode. A fourth option for the implanting physician is to insert a plug (not shown), preferably a nonconductive plug, into the lead connector bore 44, insert a setscrew (not shown) into the setscrew cavity 30 and tighten it down on the plug (to mechanically stabilize the plug), and insert the seal screw 82 into the case-activation setscrew cavity 36, in which case, neither the can 12 nor a lead electrode is activated.

With additional reference now to FIG. 1, the implanting physician has the same electrode configuration options with respect to the case-activation switch assembly (not shown) located opposite the case-activation switch assembly 34, except that the opposite case-activation switch assembly is of the opposite polarity. Otherwise stated, the opposite case-activation switch assembly is electrically coupled to the high voltage output terminal of the pulse generator circuitry of the implantable cardiac stimulation device 10 whose polarity is the opposite of the high voltage output terminal of the pulse generator circuitry to which the case-activation switch assembly 34 is electrically coupled. In this regard, with the implantable cardiac stimulation device 10 depicted in FIG. 1, the implanting physician can select any of the following six lead configurations:

(1) Can 12 inactive (both switch assemblies in the "OFF" condition); RV lead electrode (+); SVC lead electrode (−);

(2) Can 12 inactive (both switch assemblies in the "OFF" condition); RV lead electrode (−); SVC lead electrode (+);

(3) Can 12 active (+) (switch assembly 34 in the "ON" condition, with lead connector bore 44 plugged; the opposite switch assembly in the "OFF" condition); RV lead electrode (−);

(4) Can 12 active (+) (switch assembly 34 in the "ON" condition and the opposite switch assembly in the "OFF" condition); SVC lead electrode (+); RV lead electrode (−);

(5) Can 12 active (−) (switch assembly 34 in the "OFF" condition and the opposite switch assembly in the "ON" condition, with its lead connector bore plugged); RV lead electrode (+); and, (6) Can 12 active (−) (switch assembly 34 in the "OFF" condition and the opposite switch assembly in the "ON" condition); SVC lead electrode (−); RV lead electrode (+).

In one preferred embodiment, only a single switch assembly 34 is utilized. This reduces the flexibility of the system somewhat but eliminates the possibility of both switch assemblies being actuated to the "ON" condition and shorting out the high voltage output terminals. In this embodiment, the switch assembly 34 providing the can active (−) is preferred.

By using the system of the present invention, the implanting physician can choose the optimum electrode configuration for a given patient without having to bring two or more different defibrillators into the operating room, e.g., one having an active can and the other having an inactive can, and without requiring the manufacturer or physician to program the device.

Another advantage provided by the implantable cardiac stimulation device of the present invention is realized both during manufacture and during handling by implanting medical personnel. In a system having a permanently active can, or one that can be conventionally programmed to be active or inactive, there is the danger that the pulse generating circuitry could deliver a high voltage shock to anyone handling the device during manufacture or implant, because it is impossible to tell by visual inspection whether such a system is turned on, thus requiring interrogation using an external programming instrument or similar method. On the other hand, the pulse generator can of the present invention is not active unless a setscrew is inserted in a case-activating cavity, and tightened, as can be easily noted by visual inspection. Simply by not inserting or tightening such a case-activating setscrew, the pulse generator can is passive throughout the manufacturing process. During implant, the case-activating setscrew need not be inserted or tightened until near the end of the implant procedure. Once the case-activating setscrew is inserted and tightened, the device should be handled accordingly.

It should be noted that a defibrillator constructed in accordance with the present invention may be used with pre-existing leads. For example, if during a typical defibrillator replacement, due to end of battery life, the DFT is found to have increased in a patient having only RV and SVC electrodes, a replacement defibrillator with an active can as an additional electrode may be used with the existing leads to decrease the DFT.

Further, although various means have been disclosed hereinabove for effecting fluid-tight seals for each bore, cavity and hole in the switch assemblies, it should be understood that any other type of fluid-sealing means may be utilized in lieu of or in addition to those disclosed herein. For example, insulative separators, elastomeric membranes, viscous, nonconductive silicon grease, silicone gel, or any other suitable fluid-sealing means may be employed.

Although a presently preferred embodiment of the present invention has been described in detail hereinabove, it should be clearly understood that many variations and/or modifications of the basic inventive concepts herein taught which may appear to those skilled in the pertinent art will still fall within the spirit and scope of the present invention, as defined in the appended claims. For example, any number of case-activation switch assemblies constructed in accordance with the present invention can be employed in combination with any number and type of lead connector cavities, to thereby provide an implanting physician the choice of any desired number of different electrode configuration possibilities. In this regard, it should be readily appreciated that the implantable cardiac stimulation device of the presently preferred embodiment disclosed and depicted herein is merely illustrative, and is not limiting to the present invention, in its broader aspects.

What is claimed is:

1. A switch assembly for an implantable cardiac stimulation device, said switch assembly comprising:

a first electrically conductive connector block having a first portion and a second portion, said first portion having a bore and a first hole transverse to and connected to said bore;

an electrically insulative housing extending outwardly from said second portion of said first connector block;

an electrically conductive element disposed within said housing and electrically coupled to said first connector block;

a push block disposed within said housing, at least a portion of said push block being electrically conductive, wherein said push block is movable from a first position in which said electrically conductive portion is not in contact with said electrically conductive element, and a second position in which said electrically conductive portion is in contact with said electrically conductive element;

a second electrically conductive connector block having a second hole in communication with said push block; and, wherein said first and second connector blocks are electrically insulated from each other when said push block is in said first position, and are electrically coupled to each other when said push block is in said second position.

2. The switch assembly as set forth in claim 1, wherein said electrically conductive element disposed within said housing comprises a post.

3. The switch assembly as set forth in claim 2, wherein said push block includes a central recess, and said electrically conductive portion of said push block comprises an electrically conductive pad captured within said central recess, said push block further including a central aperture exposing at least a portion of an inner surface of said conductive pad facing said post.

4. The switch assembly as set forth in claim 3, further comprising a biasing element disposed in surrounding relationship to said post for exerting an upwardly directed biasing force against said push block which urges said push block into said first position, in the absence of an opposing force.

5. The switch assembly as set forth in claim 4, further comprising an electrically conductive connector element insertable into said second hole for moving said push block from said first position to said second position.

6. The switch assembly as set forth in claim 5, wherein: said second hole is internally threaded; and, said electrically conductive connector element comprises an externally threaded first setscrew rotatable in a first direction to tighten said first setscrew, said first setscrew being of sufficient length so that when it is tightened it drivingly engages said push block and produces a downwardly directed force to overcome said upwardly directing biasing force and effect movement of said push block from said first position to said second position, and further, said first setscrew being rotatable in a second direction to loosen said first setscrew and thereby permit said upwardly directing biasing force to effect movement of said push block from said second position to said first position.

7. The switch assembly as set forth in claim 6, wherein: said biasing element comprises an electrically conductive spring; and, said upwardly directing biasing force produces a frictional, anti-rotational engagement between the mating surfaces of the external threads of said first setscrew and the internal threads of said threaded second hole, when said first push block is in said second position, to thereby prevent loosening of said first setscrew over time and/or in response to mechanical stresses, and thus prevent inadvertent movement of said push block from said second position to said first position, and further, to ensure good electrical contact between the external threads of said first setscrew and the internal threads of said threaded second hole.

8. The switch assembly as set forth in claim 1, further comprising an electrically conductive connector element insertable into said second hole for moving said push block from said first position to said second position.

9. The switch assembly as set forth in claim 1, further comprising an electrically insulative seal screw insertable into said second hole to seal said second hole against intrusion of fluids.

10. The switch assembly as set forth in claim 4, further comprising an electrically insulative seal screw insertable into said second hole to seal said second hole against intrusion of fluids.

11. The switch assembly as set forth in claim 1, further comprising a first electrical conductor for electrically coupling said second connector block to an electrically conductive portion of a pulse generator case of the implantable cardiac stimulation device.

12. The switch assembly as set forth in claim 11, further comprising a second electrical conductor for electrically coupling said first connector block to a high voltage terminal of pulse generator circuitry housed by said pulse generator case.

13. The switch assembly as set forth in claim 6, wherein said bore of said first connector block comprises at least a distal portion of a lead connector cavity of the implantable cardiac stimulation device, and said first hole is internally threaded to receive a second setscrew which can be tightened down to contact a connector portion of a lead electrode or a plug pin inserted into said lead connector cavity.

14. The switch assembly as set forth in claim 9, wherein said seal screw includes a central recess and a metal insert captured by said central recess, said metal insert being adapted to receive a distal portion of a torque wrench to facilitate tightening of said seal screw.

15. An implantable cardiac stimulation device, comprising:

a pulse generator case at least a portion of which is electrically conductive;

pulse generator circuitry housed in said case;

a header attached to said case, said header including at least a first connector cavity; and, a first switch assembly, comprising:

a first electrically conductive connector block having a first portion and a second portion, said first portion having a first bore axially aligned and in communication with said first connector cavity;

a first electrically insulative housing extending outwardly from said second portion of said first connector block;

a first electrically conductive element disposed within said first housing and electrically coupled to said first connector block;

a first push block disposed within said first housing, at least a portion of said first push block being electrically conductive, wherein said first push block is movable from a first position in which said electrically conductive portion is not in contact with said first electrically conductive element, and a second position in which said electrically conductive portion is in contact with said first electrically conductive element;

a second electrically conductive connector block having a first hole in communication with said first push block; and, wherein said first and second connector blocks are electrically insulated from each other when said first push block is in said first position, and are electrically coupled to each other when said first push block is in said second position.

16. The implantable cardiac stimulation device as set forth in claim 15, wherein said first connector cavity comprises a unipolar defibrillation lead connector cavity and said first connector block includes a second hole transverse to and connected to said first bore.

17. The implantable cardiac stimulation device as set forth in claim 15, wherein said header further includes a second connector cavity, and further comprising a second switch assembly, said second switch assembly comprising:

a third electrically conductive connector block having a first portion and a second portion, said first portion of said third connector block having a second bore axially aligned and in communication with said second connector cavity;

a second electrically insulative housing extending outwardly from said second portion of said third connector block;

a second electrically conductive element disposed within said second housing and electrically coupled to said third connector block;

a second push block disposed within said second housing, at least a portion of said second push block being electrically conductive, wherein said second push block is movable from a first position in which said electrically conductive portion thereof is not in contact with said second electrically conductive element, and a second position in which said electrically conductive portion thereof is in contact with said second electrically conductive element;

a fourth electrically conductive connector block having a third hole in communication with said second push block; and, wherein said third and fourth connector blocks are electrically insulated from each other when said second push block is in said first position, and are electrically coupled to each other when said second push block is in said second position.

18. The implantable cardiac stimulation device as set forth in claim 17, wherein said first and second connector cavities comprise first and second unipolar defibrillation lead cavities of opposite polarity, respectively and said first connector block includes a second hole transverse to and connected to said first bore and a fourth hole transverse to and connected to said second bore.

19. The implantable cardiac stimulation device as set forth in claim 17, wherein said first and second switch assemblies each further comprise a biasing element disposed in said respective first and second housings for exerting an upwardly directed biasing force against said respective first or second push block which urges said respective first or second push block into said first position, in the absence of an opposing force.

20. The implantable cardiac stimulation device as set forth in claim 18, wherein said header includes front and back opposing sides and wherein said first switching assembly intersects said front side of said header and second switching assembly intersects said opposing back side of said header.

21. The implantable cardiac stimulation device as set forth in claim 17, further comprising:
   a first electrical conductor for electrically coupling said first connector block to a first high voltage terminal of said pulse generator circuitry;
   a second electrical conductor for electrically coupling said second connector block to said conductive portion of said pulse generator case;
   a third electrical conductor for electrically coupling said third connector block to a second high voltage terminal of said pulse generator circuitry; and,
   a fourth electrical conductor for electrically coupling said fourth connector block to said conductive portion of said pulse generator case.

22. A switch assembly for an implantable cardiac stimulation device, comprising:
   an electrically conductive block having a hole, said block being electrically coupled to a conductive portion of a pulse generator case of the implantable cardiac stimulation device;
   an electrically insulative housing secured to said block, said housing having an interior cavity in communication with said hole;
   an electrically conductive fixed contact element secured within said housing, said fixed contact element being electrically coupled to an output voltage terminal of pulse generator circuitry of the implantable cardiac stimulation device;
   a movable contact element disposed within said housing, at least a portion of said movable contact element being electrically conductive, said movable contact element being movable from a first position in which said electrically conductive portion thereof is not in contact with said fixed contact element, and a second position in which said electrically conductive portion thereof is in contact with said fixed contact element; and,
   wherein the pulse generator case of the implantable cardiac stimulation device is electrically activated when said movable contact element is in said second position, and is electrically inactivated when said movable contact element is in said first position.

23. The switch assembly as set forth in claim 22, wherein said fixed contact element comprises a post.

24. The switch assembly as set forth in claim 23, wherein said movable contact element comprises a push block, and said electrically conductive portion of said movable contact element comprises an electrically conductive pad captured within said central recess, said push block further including a central aperture exposing at least a portion of an inner surface of said conductive pad facing said post.

25. The switch assembly as set forth in claim 24, further comprising a resilient biasing element disposed in surrounding relationship to said post for exerting an upwardly directed biasing force against said push block which urges said push block in said first position, in the absence of an opposing force.

26. The switch assembly as set forth in claim 22, further comprising a resilient biasing element disposed in surrounding relationship to said fixed contact element for exerting an upwardly directed biasing force against said movable contact element which urges said movable contact element in said first position, in the absence of an opposing force.

27. The switch assembly as set forth in claim 26, further comprising an electrically conductive connector element insertable into said hole for moving said movable contact element from said first position to said second position.

28. A switch assembly for an implantable cardiac stimulation device, said switch assembly comprising:
   a first electrically conductive connector block;
   an electrically insulative housing extending outwardly from said first connector block;
   an electrically conductive element disposed within said housing and electrically coupled to said first connector block;
   a push block disposed within said housing, at least a portion of said push block being electrically conductive, wherein said push block is movable from a first position in which said electrically conductive portion is not in contact with said electrically conductive element, and a second position in which said electrically conductive portion is in contact with said electrically conductive element;
   a second electrically conductive connector block having a hole in communication with said push block; and,
   wherein said first and second connector blocks are electrically insulated from each other when said push block is in said first position, and are electrically coupled to each other when said push block is in said second position.

29. The switch assembly as set forth in claim 28, further comprising a biasing element disposed in said housing for exerting an upwardly directed biasing force against said push block which urges said push block into said first position, in the absence of an opposing force.

30. The switch assembly as set forth in claim 29, further comprising an electrically conductive connector element insertable into said second hole for moving said push block from said first position to said second position.

* * * * *